United States Patent
Luce

(10) Patent No.: US 7,909,765 B2
(45) Date of Patent: Mar. 22, 2011

(54) METHOD AND APPARATUS FOR DETERMINING TRUE INTRAOCULAR PRESSURE

(75) Inventor: David A. Luce, Clarence Center, NY (US)

(73) Assignee: Reichert, Inc., Depew, NY (US)

( * ) Notice: Subject to any disclaimer, the term of this patent is extended or adjusted under 35 U.S.C. 154(b) by 182 days.

(21) Appl. No.: 12/335,566

(22) Filed: Dec. 16, 2008

(65) Prior Publication Data

US 2009/0093698 A1    Apr. 9, 2009

Related U.S. Application Data

(62) Division of application No. 11/222,166, filed on Sep. 8, 2005, now Pat. No. 7,481,767.

(51) Int. Cl.
*A61B 3/16* (2006.01)
(52) U.S. Cl. ........................................ 600/405
(58) Field of Classification Search ........... 600/398–405
See application file for complete search history.

(56) References Cited

U.S. PATENT DOCUMENTS

| | | | |
|---|---|---|---|
| 5,474,066 A | 12/1995 | Grolman | |
| 6,419,631 B1 | 7/2002 | Luce | |
| 6,817,981 B2 | 11/2004 | Luce | |
| 6,875,175 B2 | 4/2005 | Luce | |
| 2004/0002640 A1* | 1/2004 | Luce | 600/399 |
| 2004/0183998 A1 | 9/2004 | Luce | |
| 2006/0015090 A1 | 1/2006 | Roberts et al. | |

OTHER PUBLICATIONS

Zadok, et al.; Pneumotonometry versus Goldmann tonometry after laser in situ keratomileusis for myopia; Journal of Cataract & Refractive Surgery, vol. 25, Issue 10, Oct. 1999; pp. 1344-1348; (http://www.sciencedirect.com/science/article/B6VSF-3XH36JX-R/2/2f2224f265a7d2eb0dfle54.
Zeimer Ophthalmic Systems AG; Pascal Dynamic Contour Tonometer; Product Literature published Jan. 3, 2005.

* cited by examiner

*Primary Examiner* — Max Hindenburg
*Assistant Examiner* — Jonathan M Foreman
(74) *Attorney, Agent, or Firm* — Hodgson Russ LLP

(57) ABSTRACT

A method and apparatus for measuring intraocular pressure of an eye use an empirically derived function wherein an inward applanation pressure P1 and an outward applanation pressure P2 obtained during a corneal deformation cycle caused by a fluid pulse are separately weighted so as to minimize cornea-related influence on the intraocular pressure value calculated by the function. In one embodiment, the function is optimized, at least in part, to minimize change in calculated IOP between measurements made before surgical alteration of the cornea and measurements made after surgical alteration of the cornea.

7 Claims, 7 Drawing Sheets

METHOD AND APPARATUS FOR DETERMINING TRUE INTRAOCULAR PRESSURE

CROSS REFERENCE TO RELATED APPLICATIONS

The present application claims benefit under 35 USC §120 as a divisional application of copending U.S. application Ser. No. 11/222,166 filed Sep. 8, 2005, now U.S. Pat. No. 7,481,767.

FIELD OF THE INVENTION

The invention relates generally to the field of ophthalmology, and more specifically to a method and apparatus for providing an intraocular pressure (IOP) measurement that is substantially independent of corneal effects, whereby the measured IOP value approaches true IOP.

BACKGROUND OF THE INVENTION

Tonometers for measuring IOP were originally developed as "contact" type instruments, meaning that a portion of the instrument is brought into contact with the cornea during the measurement procedure. A well-known instrument of this type is the Goldmann applanation tonometer (GAT) originally developed during the 1950s. The GAT measures the force required to flatten ("applanate") a known area of the cornea, and is used today as a standard against which other types of tonometers are compared to assess measurement accuracy.

Patient discomfort caused by contact tonometers such as the GAT led to the development of "non-contact" tonometers (NCTs) which operate by directing an air pulse at the patient's cornea to cause applanation. As the cornea is deformed by the fluid pulse, an opto-electronic system monitors the cornea by detecting corneally reflected light from a beam obliquely incident upon the cornea, and a peak detector signal occurs at the moment of applanation when the reflecting surface of the cornea is flat.

In state of the art NCTs, a pressure transducer measures the pump plenum pressure as the pulse is generated to provide a plenum pressure signal, whereby the plenum pressure at the moment applanation is achieved (indicated by a sharp peak in the applanation signal) can be determined. The plenum pressure at applanation is then converted to an IOP value in units of millimeters mercury (mmHg) using a linear regression equation stored during instrument clinical calibration relative to GAT as a reference. A primary index of an NCT's reliability is the standard deviation of differences $S_d$ of matched pairs of NCT and GAT clinical readings.

Current NCTs provide reasonably reliable IOP measurements, however recent studies indicate that corneal effects can have a significant impact on conventional NCT readings. This is not surprising, given that the cornea must be acted upon during the pressure measurement process and the air pulse must expend some of its energy "bending" the corneal tissue itself. Consequently, IOP readings are falsely inflated to a degree that varies from patient to patient depending upon the physical properties and characteristics of the patient's cornea at the time of measurement, such as thickness, hydration, and intrinsic tissue properties. True IOP is independent of the properties of the cornea.

During a non-contact IOP measurement, the cornea is deformed from its original convex state through a first state of applanation to a slightly concave state, and is allowed to return from concavity through a second state of applanation to convexity as the air pulse decays. Indeed, a second peak corresponding to the second state of applanation is known to occur in an applanation signal. U.S. Pat. No. 6,419,631 describes a non-contact tonometry method in which both a first plenum pressure P1 and a second plenum pressure P2 are used to calculate IOP. In one disclosed embodiment, a first IOP value ($IOP_1$) is calculated by inputting P1 to a stored regression equation derived from a plot of clinical GAT measurements against P1 measurements for a population of eyes, a second IOP value ($IOP_2$) is calculated by inputting P2 to another stored regression equation derived from a plot of clinical GAT measurements against P2 measurements for a population of eyes, and the two IOP values (IOP1 and IOP2) are averaged to yield a final result. In another disclosed embodiment, the pressures P1 and P2 are averaged and the result is input to a single stored regression equation derived from a plot of clinical GAT measurements against the average of P1 and P2 as measured for a population of eyes. A recent study of pre- and post-LASIK eyes demonstrates an unexpectedly large change in IOP after LASIK surgery when IOP is calculated according to this method, evidence that corneal effects continue to influence IOP measurement.

U.S. Pat. No. 6,817,981 describes a measurement approach intended to identify eyes having above-normal intraocular pressure. Under this approach, a standard NCT measurement of IOP is made and corneal hysteresis associated with the IOP measurement is found by calculating a pressure difference between the inward applanation pressure P1 and the outward applanation pressure P2. The standard IOP measurement value and the corneal hysteresis define a point in two-dimensional space. The location of the point is then compared to a normality line or curve in the two-dimensional space defined by data points from a statistically significant population of eyes, whereby a difference of the measured IOP from an expected IOP for a given corneal hysteresis value can be observed.

The PASCAL® Dynamic Contour Tonometer developed by SMT Swiss Microtechnology AG is a contact tonometer designed to measure true IOP. The PASCAL® tonometer comprises a concave sensor tip intended to match the convex contour of the cornea. The sensor tip is spring loaded to provide constant appositional force to the cornea, and includes a solid state piezoresistive pressure sensor for continuously measuring IOP.

SUMMARY OF THE INVENTION

It is thus an object of the present invention to provide a non-contact tonometer capable of measuring true IOP. A related object of the invention is to measure true IOP by evaluating measurement results obtained using existing NCT technology in a novel manner.

These and other objects are achieved generally by a method of measuring intraocular pressure comprising the steps of A) directing a fluid pulse at a cornea to cause reversible deformation of the cornea from an original state of convexity through a first state of applanation to a state of concavity, and back through a second state of applanation to the state of convexity; B) acquiring a first pressure value (P1) associated with the fluid pulse at a time of the first state of applanation and a second pressure value (P2) associated with the fluid pulse at a time of the second state of applanation; and C) calculating an intraocular pressure value using a predetermined function of the first pressure value (P1) and the second pressure value (P2), wherein the function was empirically derived to minimize cornea-related influence on the intraocular pressure value. In an embodiment of the present invention, the empirically derived function is expressible as $$IOP = K_1 * (F * P1 + P2) + K_2$$

wherein $F \neq -0.43$, and $K_1$ and $K_2$ are constants.

The invention also comprises a non-contact tonometer programmed to carry out the method using the empirically derived function, which may be stored in instrument memory.

The invention further provides a method of deriving a function for calculating intraocular pressure generally comprising the steps of A) referencing empirical data taken with respect to a plurality of eyes, the empirical data measuring a first pressure value (P1) associated with a first applanation of a cornea during a reversible deformation of the cornea and a second pressure value (P2) associated with a second applanation of the cornea during the reversible deformation, the first and second pressure vales (P1 and P2) being obtained both before and after surgical alteration of the cornea for each of the plurality of eyes; B) choosing a form of the function wherein the first pressure value (P1) and the second pressure value (P2) are independently weighted variables; and C) determining relative weights of the first and second pressure values (P1 and P2) so as to minimize change in the intraocular pressure value between measurements made before surgical alteration of the cornea and measurements made after surgical alteration of the cornea.

BRIEF DESCRIPTION OF THE DRAWINGS

The nature and mode of operation of the present invention will now be more fully described in the following detailed description taken with the accompanying drawing figures, in which.

DETAILED DESCRIPTION OF THE INVENTION

Figure 1:
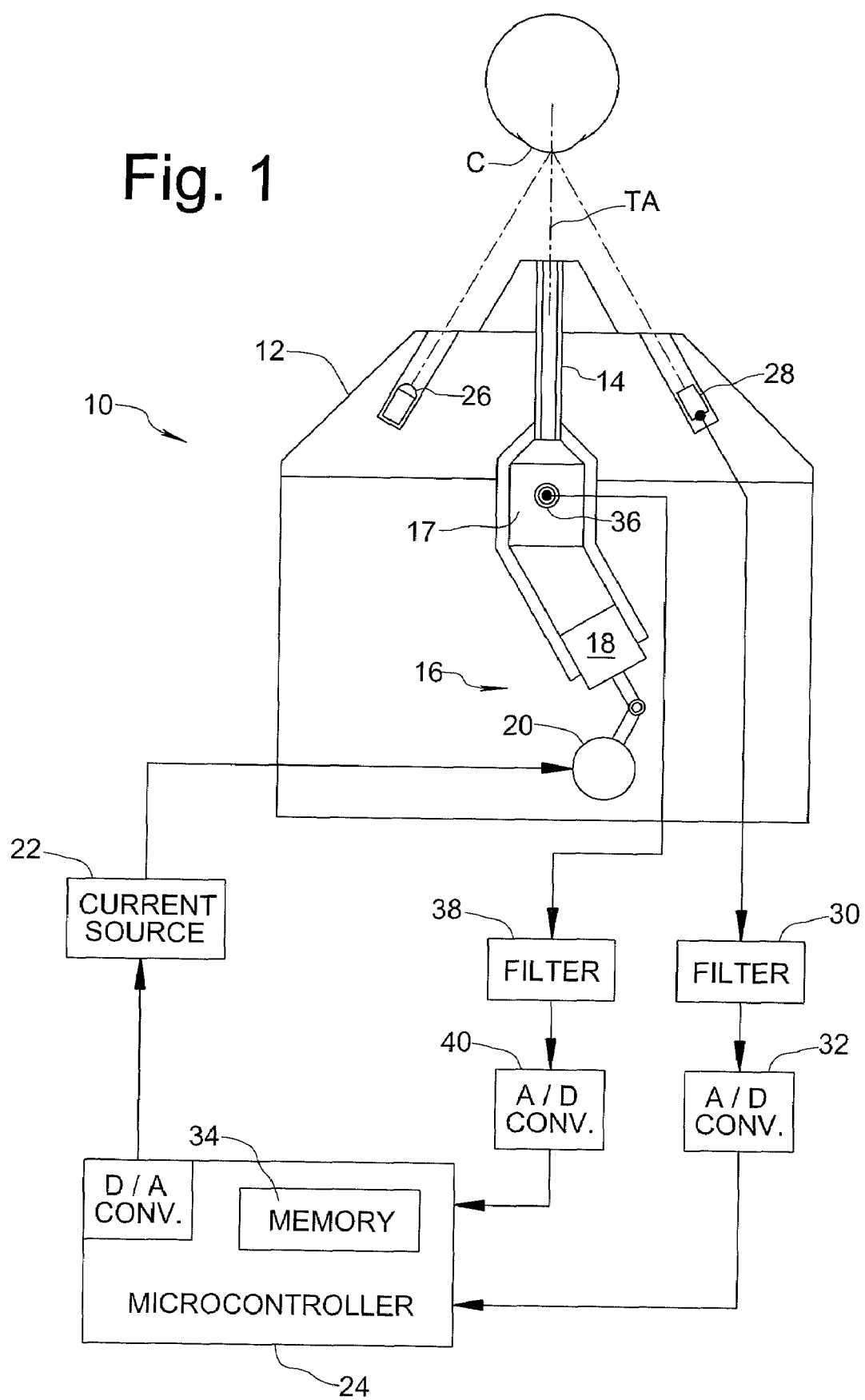
FIG. 1 is a schematic view of an NCT embodying the present invention.

FIG. 1 shows a non-contact tonometer 10 in schematic view. A test portion of NCT 10 is depicted as generally including a nosepiece 12 in which a fluid discharge tube 14 is fixed. The fluid discharge tube 14 defines a test axis TA that is aligned with a vertex of cornea C when measurement is carried out. The test portion of NCT 10 further includes a pump mechanism 16 having a plenum chamber 17 in flow communication with an entry end of fluid discharge tube 14, a piston 18 movable to compress fluid within plenum chamber 17, and a drive motor 20 connected to the piston. As will be familiar to persons skilled in the art of non-contact tonometry, the pump mechanism 16 is operable to rapidly increase fluid pressure within plenum chamber 17, thereby generating a fluid pulse that is discharged from an exit end of fluid discharge tube 14 in the direction of cornea C to cause deformation of the cornea. In the depicted embodiment, motor 20 is energized by a current source 22 in response to a command signal from a microcontroller 24. As used herein, the term "microcontroller" means any integrated circuit that includes at least a central processing unit (CPU) and a memory. The memory preferably includes a non-volatile memory device for retaining stored information when power is turned off. Suitable non-contact tonometers for practicing the present invention include, but are not limited to, the AT-555 Non-Contact Tonometer and the Ocular Response Analyzer (ORA) manufactured by Reichert, Inc., assignee of the present application.

Figure 2A:
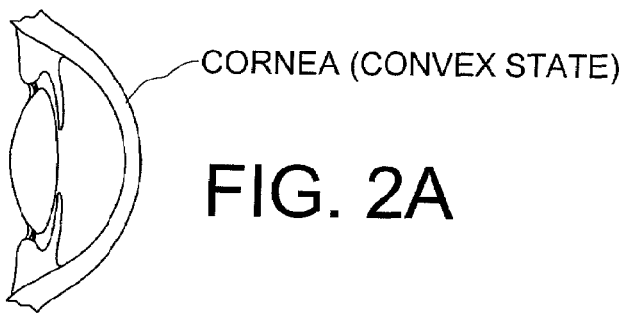
FIGS. 2A through 2E are a sequential series of views showing stages of deformation of a cornea during measurement of IOP in accordance with a method of the present invention.
Figure 2B:
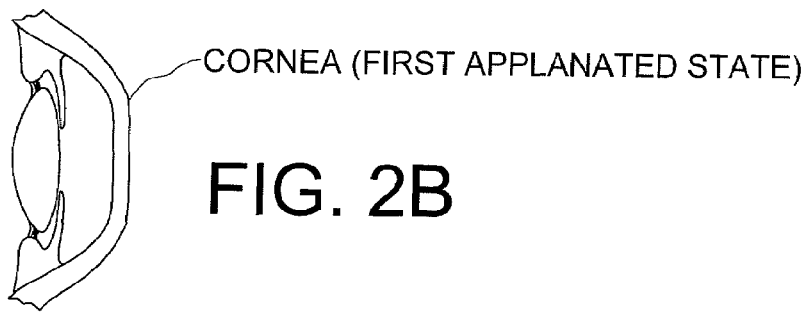
Figure 2C:
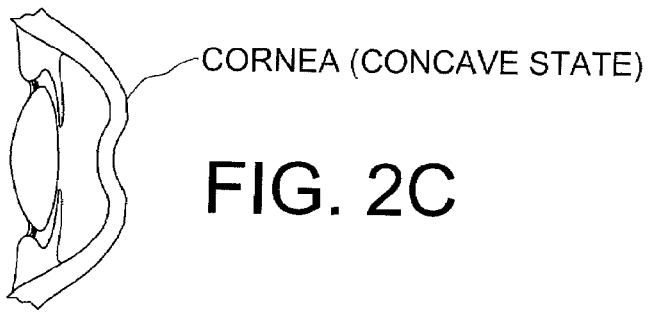

FIGS. 2A-2E show a corneal deformation cycle caused by the fluid pulse. FIG. 2A shows cornea C in its original and natural convex state. FIG. 2B shows cornea C in a first state of applanation as the cornea is pushed inwardly by the fluid pulse, and FIG. 2C shows cornea C in a concave state as the air pulse pushes the corneal tissue beyond its flattened state of FIG. 2B. The air pulse then decays and the cornea is allowed to pass through a second state of applanation, shown in FIG. 2D, as the cornea deforms in an outward direction to return to its original and natural convex state depicted again in FIG. 2E.

Corneal deformation may be monitored by an optoelectronic monitoring system such as that shown in FIG. 1, wherein a light source 26 is obliquely aimed at the cornea, and a photosensitive detector 28 is arranged on an opposite side of the test axis TA to receive corneally reflected light. As will be understood, when cornea C is convex (FIGS. 2A, 2E) or concave (FIG. 2C), a beam from light source 26 will become fanned out after reflection by the curved corneal surface and the signal generated by photosensitive detector 28 will be relatively weak. However, when cornea C is in an applanated state (FIGS. 2B and 2D), the light beam from light source 26 remains well-defined after reflection by the flattened corneal surface such that more light reaches photosensitive detector 28 and a peak signal is generated by the detector. The signal information generated by photosensitive detector 28 during the corneal deformation cycle, referred to herein as the "applanation signal," is processed by a filter 30, converted to digital form by analog-to-digital converter 32, and input to microcontroller 24 where it may be stored by memory 34. An applanation signal from a typical NCT measurement is plotted in FIG. 3, and includes a pair of well-defined signal peaks A1 and A2 corresponding to a first applanation event during inward deformation of cornea C (see FIG. 2B) and a second applanation event during outward deformation of cornea C (see FIG. 2D), respectively.

The pressure within plenum chamber 17 is also monitored during the corneal deformation cycle. In the embodiment shown, a pressure sensor 36 is positioned in plenum chamber 17 near the entry end of fluid discharge tube 14 to generate signal information representative of the plenum pressure associated with the fluid pulse. The signal information generated by pressure sensor 36 is processed by a filter 38, converted to digital form by analog-to-digital converter 40, and input to microcontroller 24 where it may be stored by memory 34. A pressure signal from an NCT measurement according to the invention is plotted in FIG. 3, and is characterized by a Gaussian bell curve shape. It is preferable to adjust the parameters of pump mechanism 16 to provide a pressure signal that is at least approximately symmetrical about a moment in time and has a suitable spread, whereby a first pressure P1 coinciding with first applanation A1 and a second pressure P2 coinciding with second applanation A2 may be accurately determined by evaluating the applanation and pressure signals. For example, parameters that may be adjusted to optimize the shape of the pressure signal as a function of time include the weight of piston 18 and the time profile of the energizing current delivered by current source 22 to motor 20. Evaluation of the applanation signal and pressure signal is performed by microcontroller 24.

Figure 2D:
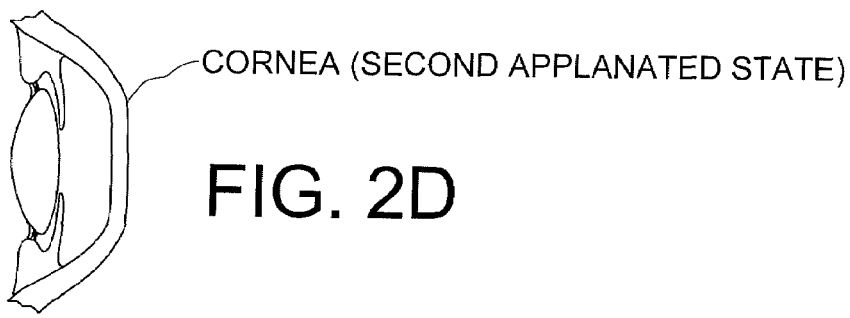
Figure 2E:
Figure 3:
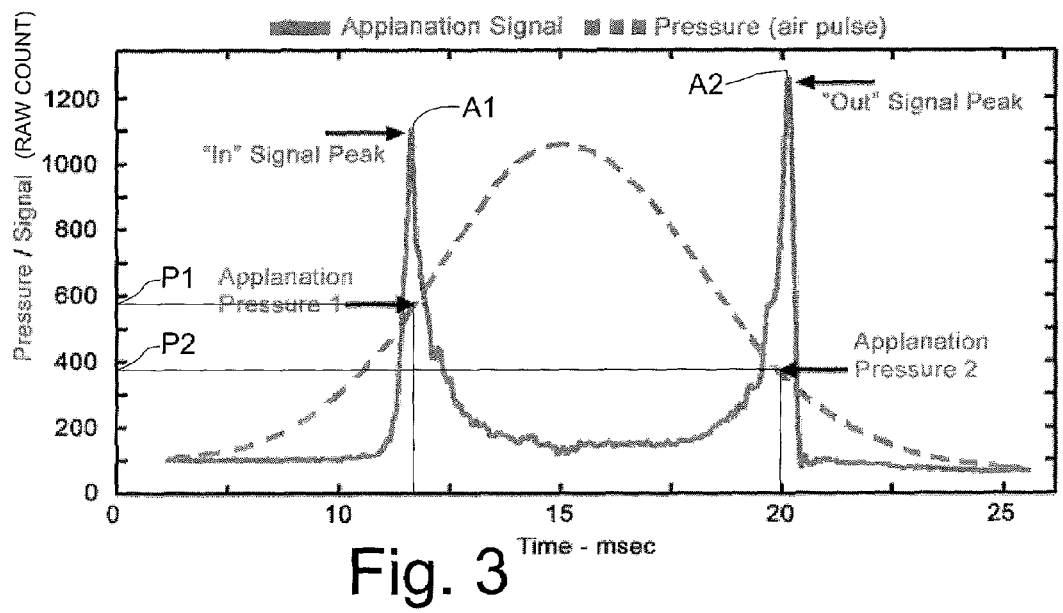
FIG. 3 is a graph showing an applanation signal and a plenum pressure signal during an NCT measurement in accordance with the present invention.

Thus, during a single corneal deformation cycle, two digital pressure values are obtained corresponding to the detected plenum pressure at the time of inward applanation (FIG. 2B) and at the time of outward applanation (FIG. 2D). For purposes of this specification, the first or inward pressure value is denoted P1, and the second or outward pressure value is denoted P2. The pressure values P1 and P2 are expressed in raw form as a digital "count" proportional to the amplitude of the pressure signal generated by pressure sensor 36.

Based on analysis of data from various clinical trials, it was observed that pressure values P1 and P2 respond independently to various factors such as central corneal thickness, surgical alteration of the cornea, and clinically induced changes in IOP. Therefore, in accordance with the present invention, an "optimum combination" of the two independent parameters P1 and P2 was sought to yield the best IOP value.

More specifically, a function for calculating IOP from pressure values P1 and P2 was empirically derived from clinical data, wherein the function was optimized so as to minimize cornea-related influence on the calculated IOP value. In a current embodiment, clinical data comprising plenum pressure values P1 and P2 measured both before and after surgical alteration of the cornea in a plurality of eyes were used. The clinical data involved measurements taken before and after LASIK (Laser-Assisted In Situ Keratomileusis) surgery and are set forth in Table I below.

TABLE I

| Pre-LASIK | | Post-LASIK | |
|---|---|---|---|
| $P1_{bef}$ (raw count) | $P2_{bef}$ (raw count) | $P1_{aft}$ (raw count) | $P2_{aft}$ (raw count) |
| 249 | 168 | 203 | 147 |
| 247 | 166 | 196 | 141 |
| 269 | 181 | 209 | 149 |
| 286 | 194 | 197 | 152 |
| 200 | 111 | 179 | 105 |
| 210 | 128 | 182 | 114 |
| 229 | 175 | 182 | 146 |
| 231 | 158 | 197 | 154 |
| 246 | 171 | 217 | 163 |
| 227 | 146 | 187 | 123 |
| 227 | 139 | 175 | 111 |
| 257 | 148 | 177 | 120 |

In addition to the data shown in Table I above, further clinical data giving P1, P2, and central corneal thickness (CCT) for various populations of eyes were used.

The function for calculating IOP was assumed to be a linear combination of pressure values P1 and P2, and optimization was based on i) minimizing the difference between reported IOP measured before surgical alteration of the cornea and reported IOP measured after surgical alteration of the cornea, since theoretically, the corneal alteration should have essentially no effect on true IOP; and ii) minimizing statistical correlation between reported IOP and central corneal thickness, since true IOP is independent of central corneal thickness. As used herein, the term "minimize" and its alternate forms are used in a broad sense to include reducing a parameter.

Without loss of generality, the linear function for calculating IOP can be written $$IOP = K_1 * (F * P1 + P2) + K_2 \quad (1)$$

wherein "$K_1$" is slope, "$K_2$" is an offset determined by properties of the NCT measurement apparatus that influence the pressure signal, and "F" is a scale factor weighting P1 relative to P2.

Thus, the task of optimizing the above IOP function involves finding the value of scale factor F that minimizes the absolute value of the difference between pre-surgery and post-surgery IOP as calculated by the function. The value of F may be approximated by plotting $\Delta IOP$, defined as $$\Delta IOP = |(F * P1_{aft} + P2_{aft}) - (F * P1_{bef} + P2_{bef})| \quad (2)$$

against scale factor F and locating the minimum, where $P1_{aft}$ is the average first pressure P1 measured post-LASIK from Table I, $P2_{aft}$ is the average second pressure P2 measured post-LASIK from Table I, $P1_{bef}$ is the average first pressure P1 measured pre-LASIK from Table I, and $P2_{bef}$ is the average second pressure P2 measured pre-LASIK from Table I. Referring to Table II below, $\Delta IOP$ is calculated at incremental values of F, and a plot corresponding to Table II is provided at FIG. 4.

TABLE II

| F | $\Delta IOP$ |
|---|---|
| 0.0 | 21.67 |
| −0.1 | 16.86 |
| −0.2 | 12.05 |
| −0.3 | 7.24 |
| −0.4 | 2.43 |
| −0.5 | 2.38 |
| −0.6 | 7.18 |
| −0.7 | 11.99 |
| −0.8 | 16.80 |
| −0.9 | 21.61 |
| −1.0 | 26.42 |

Figure 4:
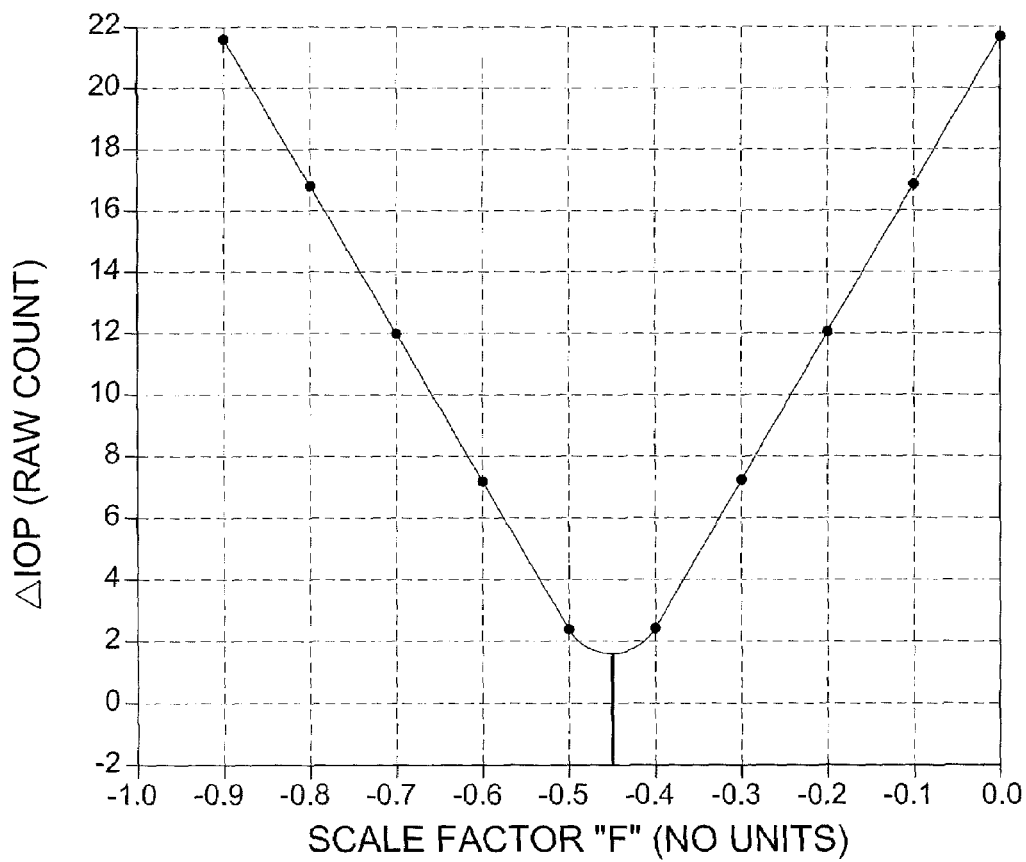
FIG. 4 is a graph in which the absolute difference between pre- and post-LASIK IOP calculations is plotted as a function of a scale factor weighting a first plenum pressure value relative to a second plenum pressure value in the function used to calculate IOP.

It is apparent from FIG. 4 that a relatively well-defined minimum in the curve occurs very close to F=−0.45.

Figure 5:
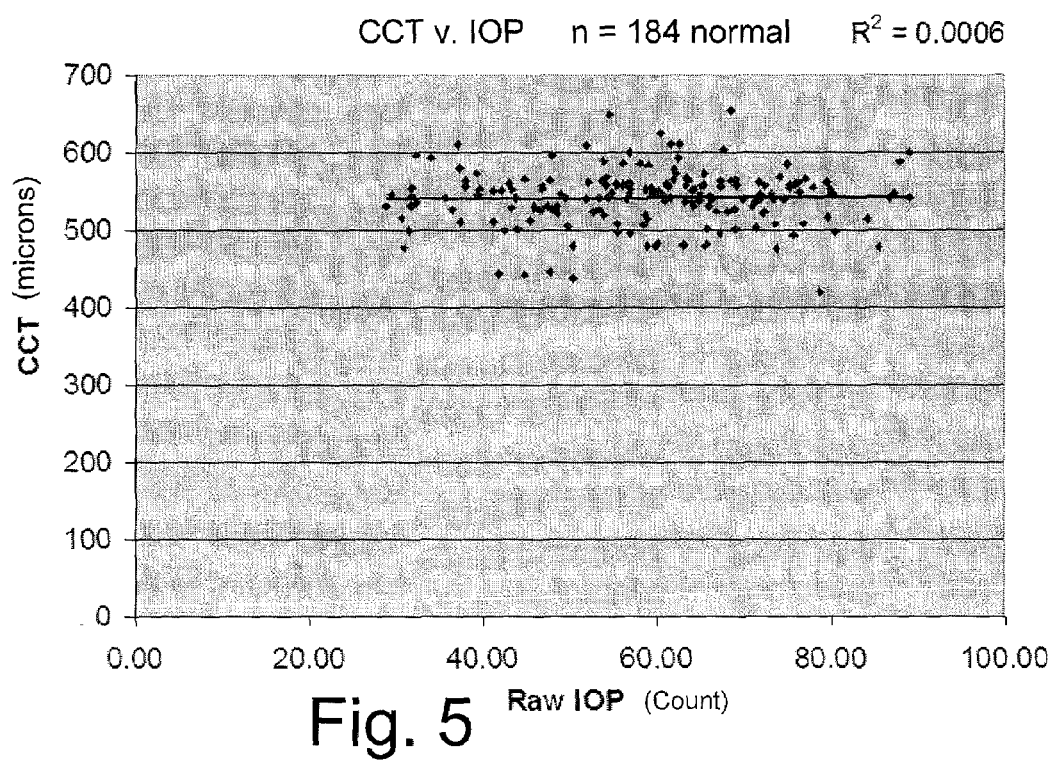
FIG. 5 is a graph of central corneal thickness versus IOP for a population of normal eyes, where IOP is calculated according to an optimized function of the present invention.
Figure 6:
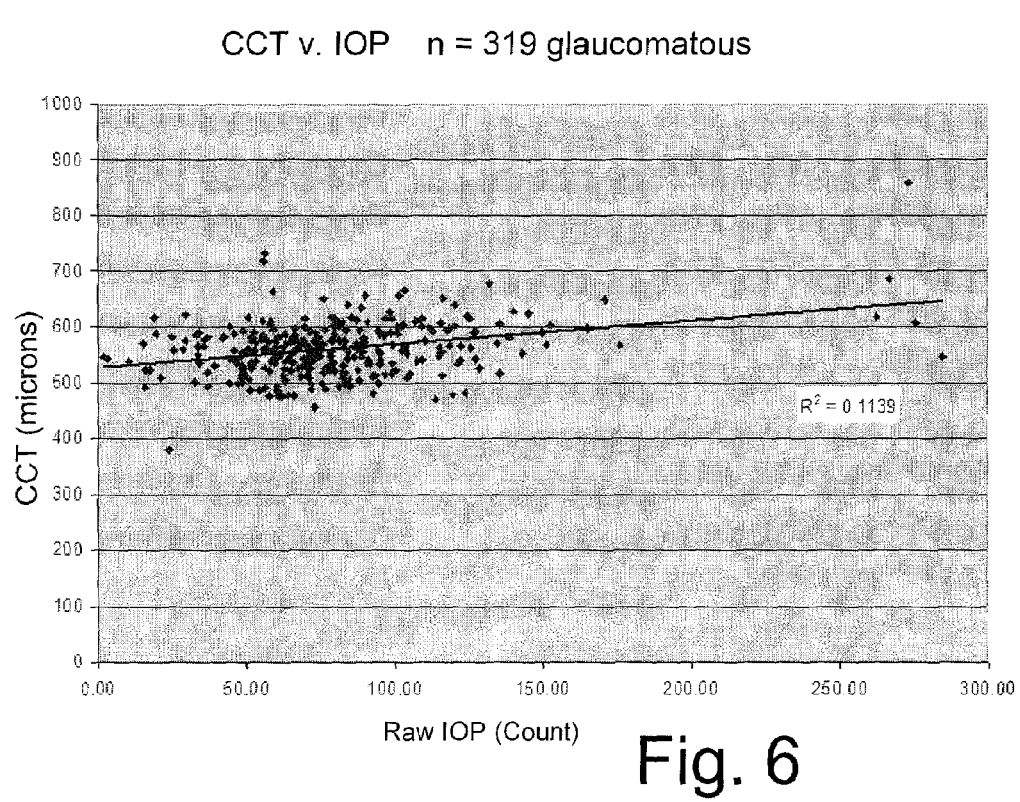
FIG. 6 is a graph of central corneal thickness versus IOP for a population of glaucomatous eyes, where IOP is calculated according to an optimized function of the present invention.
Figure 7:
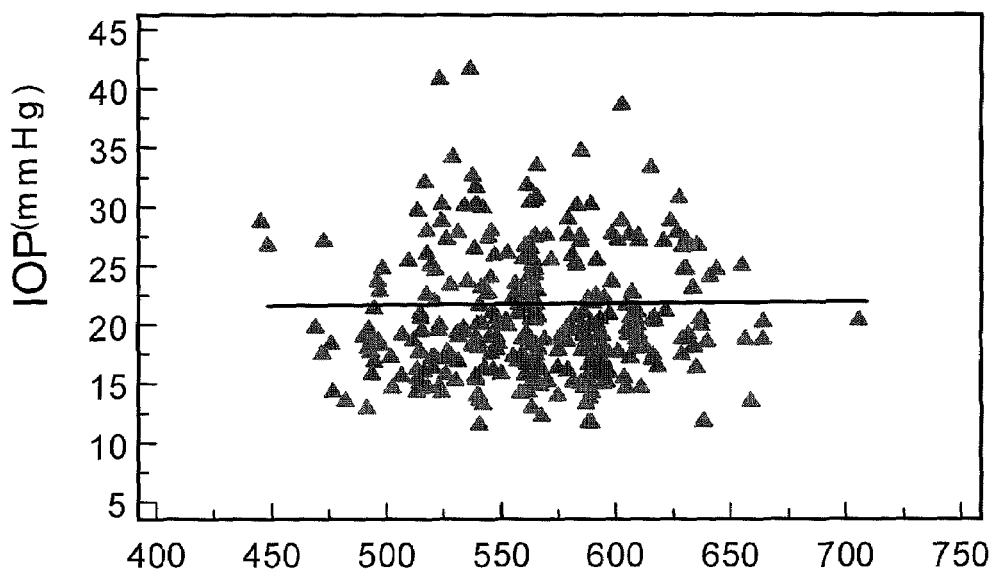
FIG. 7 is a graph of IOP versus central corneal thickness for a population of eyes both with and without Iopidine-induced IOP reduction, where IOP is calculated according to an optimized function of the present invention.

The task of optimizing the IOP function of equation (1) may additionally involve adjusting F such that correlation between calculated IOP and central corneal thickness is essentially removed. Clinical data used for this adjustment included pressure and central corneal thickness data taken on a population of 184 normal eyes, a population of 319 glaucomatous eyes, and a population of 310 eyes measured both in their natural state and a state of lowered IOP induced by administering Iopidine to the eye. By plotting statistical correlation ($R^2$) as a function of scale factor F, it was found that a scale factor F=−0.43 essentially removed all statistical correlation between IOP and central corneal thickness in the population of Iopidine eyes ($R^2$=0) and in the population of normal eyes (the population of normal eyes ($R^2$=0.0006). With respect to the population of glaucomatous eyes, a scale factor F=−0.43 resulted in a slight statistical correlation between IOP and central corneal thickness ($R^2=0.1139$). Plots demonstrating the lack of statistical correlation between calculated IOP and central corneal thickness for the three populations mentioned above are presented in FIGS. 5, 6, and 7. Accordingly, the scale factor F was empirically optimized to be −0.43, such that $$IOP=K_1*(P2-0.43*P1)+K_2 \qquad (3)$$

It is emphasized that error exists with respect to every measurement, and thus the empirically derived value of scale factor F may be expressed with an associated tolerance range. For present purposes, scale factor F=−0.43±0.1.

Figure 8:
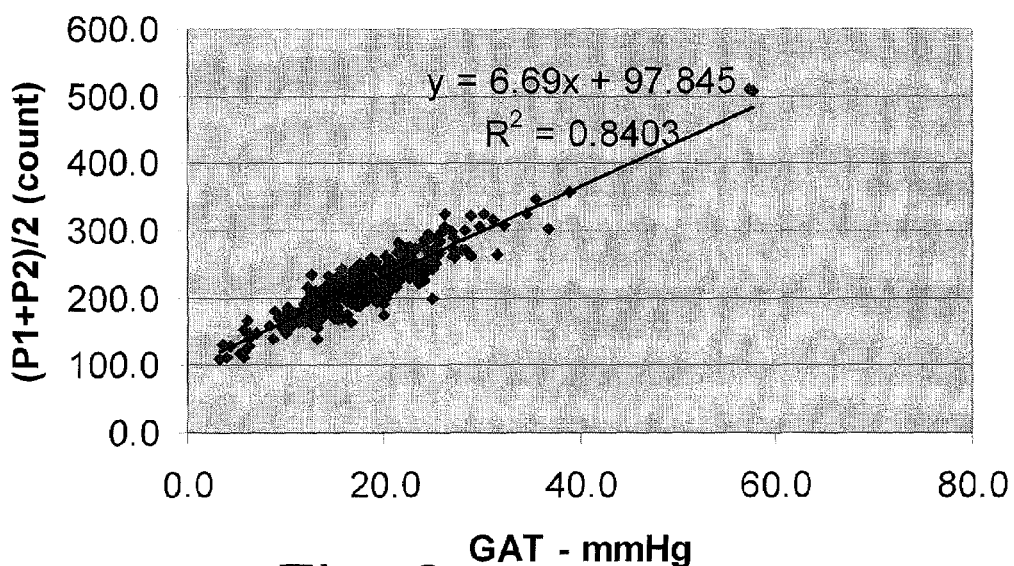
FIG. 8 is a graph of average plenum pressure versus GAT measurement values for a population of eyes.

As mentioned above, the values of $K_1$ and $K_2$ are specific to a given NCT, and therefore each NCT must be calibrated in order to provide accurate measurement results. One theoretical possibility for calibration is to determine $K_1$ and $K_2$ for each specific instrument by calibrating each instrument directly or indirectly against GAT. This may be done by measuring a plurality of eyes with GAT and measuring the same plurality of eyes with the instrument to be calibrated to obtain P1 and P2 raw count values for the same plurality of eyes. In an embodiment of the present invention, the data may then be evaluated through two regression steps. The first step is a normal linear regression of average plenum pressure (P1+P2)/2 against GAT values to find a scale factor relating pressure in arbitrary digital "count" units to an equivalent pressure in millimeters mercury and give a GAT-equivalent IOP (referred to herein as "IOPG") from pressures P1 and P2. FIG. 8 shows a plot of (P1+P2)/2 versus GAT using data from a clinical study performed at the Wilmer Eye Institute at Johns Hopkins Hospital in Baltimore, Md. The study was performed using GAT and an NCT manufactured by Reichert, Inc., owner of the present application. Data were collected on 339 eyes ranging in GAT IOP reading from 3.0 mmHg to 57.3 mmHg. Two NCT measurements per eye and three GAT measurements per eye were taken with random right/left eye selection and random GAT—NCT sequence. The data are presented in Table III appearing at the end of this Detailed Description. Mathematically, $$(P1+P2)/2=6.69*GAT+97.845 \qquad (4)$$

By definition, IOPG=GAT. Solving equation (4) for GAT provides IOPG in terms of P1 and P2 as follows:

$$IOPG=GAT=0.149*((P1+P2)/2)-15 \qquad (5)$$

The second step is an orthogonal linear regression of (P2−0.43*P1) against IOPG. By choosing scale factor K1 such that the slope becomes 1, and forcing the y-intercept through 0, $K_1$ and $K_2$ are determined such that computed IOP is correlated to IOPG and thus ultimately to GAT. The orthogonal linear regression yielded IOP in millimeters mercury as a function of P1 and P2 as follows:

$$IOP=0.225*(P2-0.43*P1)+5.16 \qquad (6)$$

wherein 5.16 is a baseline corrected offset and P1 and P2 are baseline corrected pressure count values. Equation (6) applies for the particular NCT used in the clinical study.

An alternative approach may be used based on a linear regression of (P2−0.43*P1) directly against GAT, which will provide a slightly different but acceptable result.

Of course, it is highly impractical to calibrate each NCT intended for commercial sale in this manner. Instead, in order to calibrate each commercial NCT, a "master" NCT is calibrated as described above, and the calibrated master NCT is used as a reference standard for calibrating production NCTs intended for sale to customers. This latter step is preferably performed using a tonometer calibration tool and calibration methodology as described in commonly-owned U.S. Pat. No. 6,679,842. The tonometer calibration tool is used to determine an average value of P1 (baseline corrected count) provided by the master NCT for each of three different calibration pressure settings A (low), B (medium), and C (high) of the tonometer calibration tool. These plenum pressure calibration values associated with the master NCT are designated $P1_A^M$, $P1_B^M$, and $P1_C^M$, respectively. It is then necessary to determine an average value of P1 (baseline corrected count) provided by a subject production NCT for each of the three different calibration pressure settings A (low), B (medium), and C (high) of the tonometer calibration tool. These plenum pressure calibration values associated with the production NCT are designated $P1_A^P$, $P1_B^P$, and $P1_C^P$, respectively. Then, a linear regression of the production NCT pressure values versus the master NCT pressure values is performed:

$$(P1_A^P, P1_B^P, P1_C^P) = m_{ABC}*(P1_A^M, P1_B^M, P1_C^M) + b_{ABC} \qquad (7)$$

wherein $m_{ABC}$ and $b_{ABC}$ are calibration constants for the production NCT. The calibration constants $m_{ABC}$ and $b_{ABC}$ are used to convert the raw pressure values measured by a given production NCT into equivalent pressure values of the master NCT so that equation (6), derived for calculating IOP in the master NCT, is valid for calculating IOP in the production NCT. Accordingly, if the raw plenum pressure values measured by a production NCT are $P1_S$ and $P2_S$, then new calibration-converted plenum pressures $\overline{P1}_S$ and $\overline{P2}_S$ are calculated as follows:

$$\overline{P1}_S = (1/m_{ABC})*(P1_S - b_{ABC}) \qquad (8a)$$

$$\overline{P2}_S = (1/m_{ABC})*(P2_S - b_{ABC}) \qquad (8b)$$

The converted pressure values $\overline{P1}_S$ and $\overline{P2}_S$ may then be inputted to equation (6) to calculate IOP:

$$IOP = 0.225*(\overline{P2}_S - 0.43*\overline{P1}_S) + 5.16 \qquad (9)$$

Thus, the parameters $K_1$ and $K_2$ derived for calculating IOP in the master NCT based on empirical data, and the calibration parameters $m_{ABC}$ and $b_{ABC}$ used for converting raw pressure values, are stored in memory 34 of each production instrument, along with programming code for performing the calculations set forth in equations (8a), (8b) and (9) above.

Figure 9:
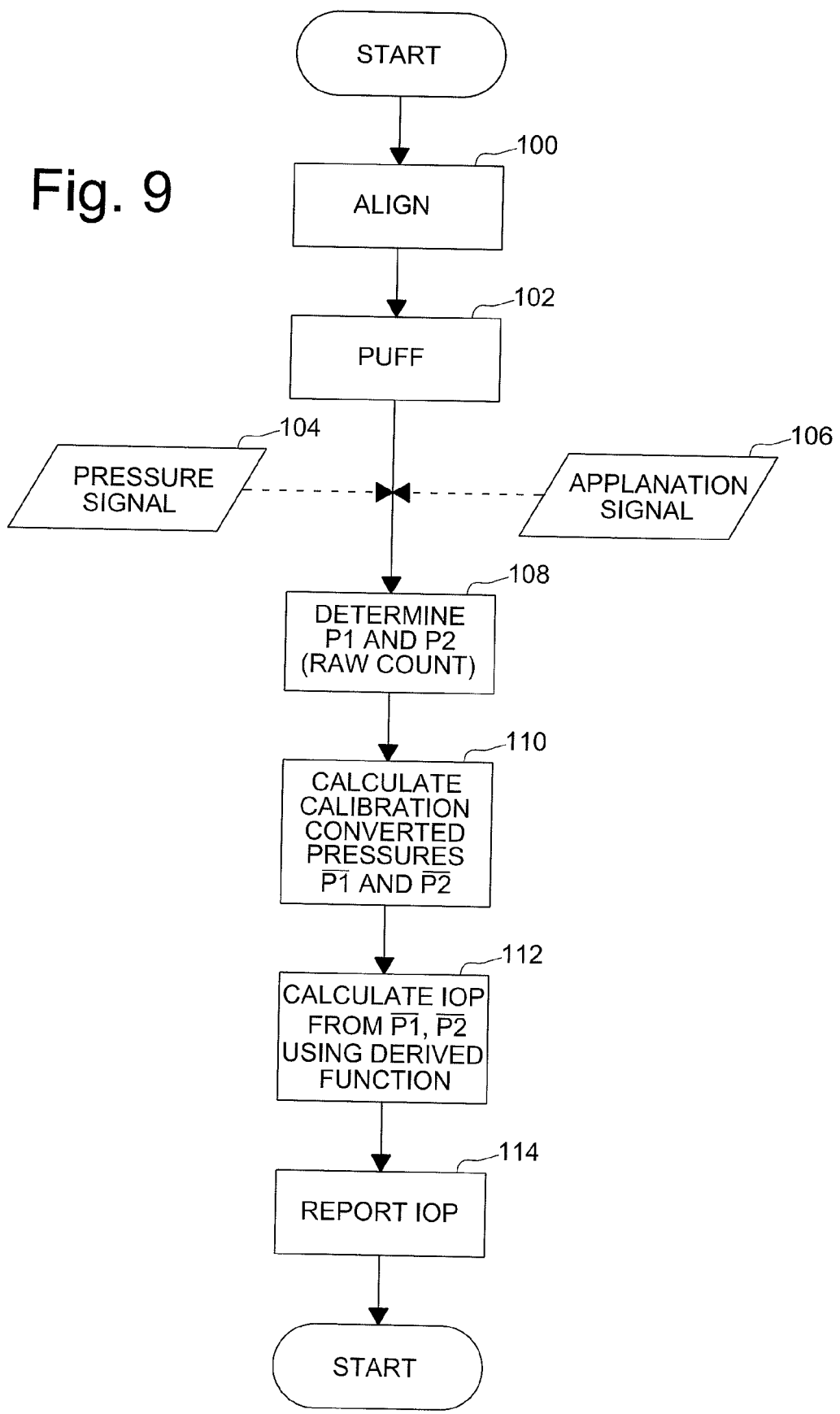
FIG. 9 is a flow chart illustrating a measurement process in accordance with an embodiment of the present invention.

FIG. 9 is a flow chart showing the measurement process carried out by an NCT calibrated and programmed in accordance with the present invention. The test axis TA of the NCT is aligned with the patient's eye in step 100, and a fluid pulse, for example an air puff, is directed at the cornea in step 102. Blocks 104 and 106 represent generation of a pressure signal and applanation signal as described above with respect to FIG. 3. In step 108, the pressure and applanation signals are digitized and the digitized signals are processed to determine pressure values P1 and P2. The pressure values P1 and P2 are adjusted in step 110 based on calibration of the instrument as described above to yield calibration corrected pressure values $\overline{P1}$ and $\overline{P2}$. In step 112 the calibration corrected pressure values $\overline{P1}$ and $\overline{P2}$ are input to the predetermined function for calculating IOP, which function may be stored in instrument memory, preferably non-volatile memory, during instrument calibration. Finally, the calculated IOP is reported in step 114, for example by displaying, printing, or audibly reporting the IOP value.

Figure 10:
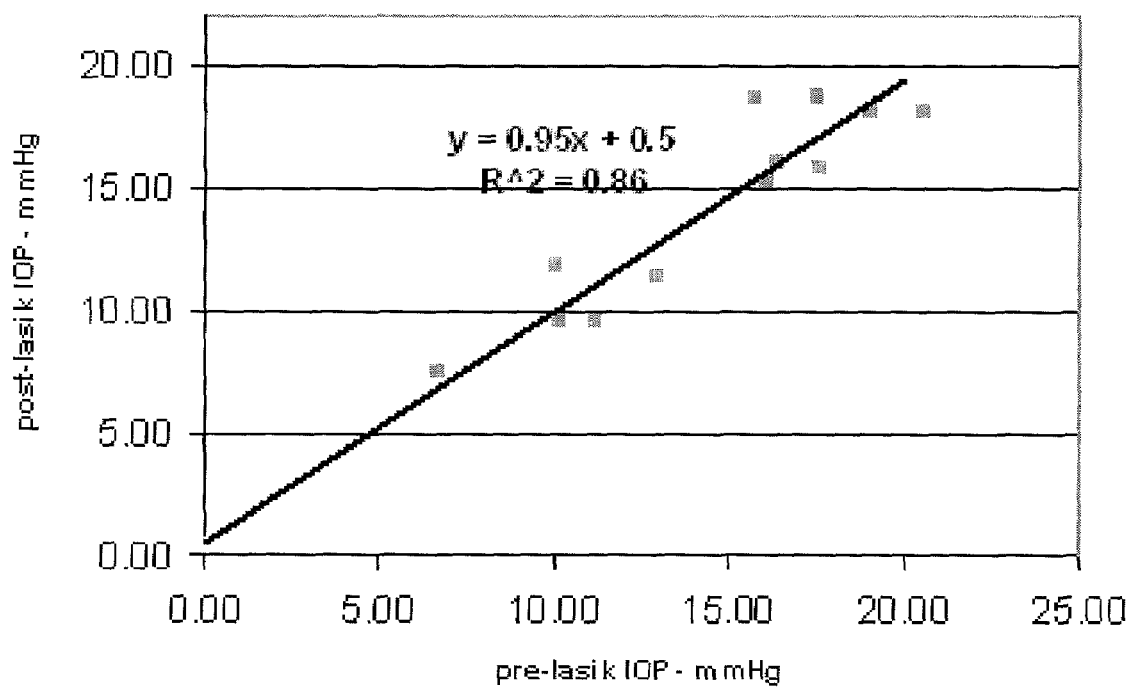
FIG. 10 is a graph showing post-LASIK IOP measurements made in accordance with the present invention plotted against pre-LASIK IOP measurements made in accordance with the present invention.

FIG. 10 demonstrates the effectiveness of the present invention with respect to the data set of Table I above. Using the optimized function of the present invention, IOP measurements in units of mmHg taken before and after LASIK surgery for the population of eyes were strongly correlated ($R^2=0.95$). As discussed above, this should be the case because each eye should have essentially constant IOP regardless of corneal shape or other corneal properties.

TABLE III

| GAT (mmHg) | CCT - (mm) | P1 - (count) | P2 - (count) | (P1 + P2)/2 (count) | P2 - .43 * P1 (count) | IOPG (mmHg) |
|---|---|---|---|---|---|---|
| 15.6 | 0.618 | 246.7 | 156.8 | 201.7 | 50.7 | 15.2 |
| 19.0 | 0.611 | 272.1 | 175.4 | 223.8 | 58.4 | 18.4 |
| 26.0 | 0.555 | 333.9 | 259.3 | 296.6 | 115.7 | 29.3 |
| 21.3 | 0.515 | 280.8 | 217.5 | 249.2 | 96.7 | 22.2 |
| 21.3 | 0.589 | 267.8 | 175.3 | 221.5 | 60.1 | 18.1 |
| 17.6 | 0.510 | 277.8 | 223.7 | 250.7 | 104.2 | 22.5 |
| 27.3 | 0.482 | 282.1 | 245.2 | 263.6 | 123.9 | 24.4 |
| 6.3 | 0.618 | 182.4 | 97.4 | 139.9 | 19.0 | 5.9 |
| 6.0 | 0.664 | 190.7 | 140.9 | 165.8 | 58.9 | 9.8 |
| 25.3 | 0.568 | 304.2 | 230.1 | 267.2 | 99.3 | 24.9 |
| 25.3 | 0.593 | 324.5 | 252.5 | 288.5 | 113.0 | 28.1 |
| 22.3 | 0.513 | 269.6 | 209.7 | 239.6 | 93.8 | 20.8 |
| 13.3 | 0.601 | 207.3 | 133.7 | 170.5 | 44.6 | 10.5 |
| 24.6 | 0.598 | 329.2 | 260.1 | 294.6 | 118.5 | 29.0 |
| 12.3 | 0.527 | 232.1 | 156.0 | 194.0 | 56.2 | 14.0 |
| 20.3 | 0.585 | 238.0 | 158.3 | 198.2 | 56.0 | 14.6 |
| 18.3 | 0.531 | 245.1 | 188.0 | 216.6 | 82.7 | 17.4 |
| 24.6 | 0.533 | 307.5 | 223.9 | 265.7 | 91.6 | 24.7 |
| 18.6 | 0.589 | 267.9 | 216.2 | 242.1 | 101.0 | 21.2 |
| 12.0 | 0.485 | 195.5 | 144.7 | 170.1 | 60.6 | 10.4 |
| 19.6 | 0.550 | 238.5 | 162.2 | 200.4 | 59.7 | 15.0 |
| 9.3 | 0.556 | 202.0 | 137.8 | 169.9 | 51.0 | 10.4 |
| 19.3 | 0.619 | 250.6 | 186.6 | 218.6 | 78.8 | 17.7 |
| 8.3 | 0.578 | 194.6 | 120.1 | 157.3 | 36.4 | 8.5 |
| 10.6 | 0.719 | 193.2 | 139.1 | 166.2 | 56.0 | 9.8 |
| 17.6 | 0.544 | 277.1 | 203.1 | 240.1 | 83.9 | 20.9 |
| 15.3 | 0.509 | 217.2 | 176.0 | 196.6 | 82.6 | 14.4 |
| 13.3 | 0.556 | 222.4 | 179.8 | 201.1 | 84.2 | 15.1 |
| 10.3 | 0.477 | 214.5 | 158.2 | 186.4 | 66.0 | 12.9 |
| 11.3 | 0.562 | 213.1 | 142.0 | 177.6 | 50.4 | 11.5 |
| 13.0 | 0.576 | 246.4 | 162.8 | 204.6 | 56.9 | 15.6 |
| 24.3 | 0.516 | 260.1 | 217.1 | 238.6 | 105.2 | 20.7 |
| 27.0 | 0.548 | 299.8 | 243.9 | 271.9 | 115.0 | 25.6 |
| 15.3 | 0.591 | 247.1 | 158.9 | 203.0 | 52.7 | 15.3 |
| 31.3 | 0.568 | 335.5 | 295.3 | 315.4 | 151.1 | 32.1 |
| 28.0 | 0.542 | 301.2 | 238.9 | 270.0 | 109.4 | 25.4 |
| 18.6 | 0.506 | 236.5 | 186.5 | 211.5 | 84.8 | 16.6 |
| 12.6 | 0.564 | 198.9 | 122.4 | 160.7 | 36.9 | 9.0 |
| 18.0 | 0.570 | 258.7 | 198.3 | 228.5 | 87.0 | 19.1 |
| 9.3 | 0.502 | 218.4 | 126.9 | 172.6 | 33.0 | 10.8 |
| 15.3 | 0.575 | 272.8 | 190.2 | 231.5 | 72.9 | 19.6 |
| 18.3 | 0.551 | 254.7 | 174.9 | 214.8 | 65.4 | 17.1 |
| 10.0 | 0.536 | 214.7 | 126.6 | 170.7 | 34.3 | 10.5 |
| 14.6 | 0.498 | 211.7 | 166.6 | 189.1 | 75.5 | 13.3 |
| 18.0 | 0.548 | 223.1 | 170.5 | 196.8 | 74.6 | 14.4 |
| 24.6 | 0.575 | 283.4 | 200.6 | 242.0 | 78.7 | 21.2 |
| 18.0 | 0.489 | 248.9 | 178.8 | 213.9 | 71.8 | 17.0 |
| 22.3 | 0.586 | 291.2 | 191.8 | 241.5 | 66.6 | 21.1 |
| 18.3 | 0.582 | 263.5 | 187.5 | 225.5 | 74.1 | 18.7 |
| 24.0 | 0.552 | 291.5 | 263.2 | 277.3 | 137.8 | 26.5 |
| 10.6 | 0.509 | 201.0 | 148.2 | 174.6 | 61.8 | 11.1 |
| 19.3 | 0.590 | 286.6 | 222.0 | 254.3 | 98.8 | 23.0 |
| 20.3 | 0.565 | 259.2 | 198.4 | 228.8 | 87.0 | 19.2 |
| 17.3 | 0.656 | 279.9 | 210.5 | 245.2 | 90.2 | 21.6 |
| 15.3 | 0.539 | 232.2 | 158.2 | 195.2 | 58.4 | 14.2 |
| 16.6 | 0.641 | 245.5 | 189.7 | 217.6 | 84.1 | 17.5 |
| 11.3 | 0.498 | 201.8 | 133.7 | 167.7 | 46.9 | 10.1 |
| 15.6 | 0.571 | 247.8 | 171.3 | 209.5 | 64.7 | 16.3 |
| 18.6 | 0.556 | 252.2 | 166.7 | 209.4 | 58.2 | 16.3 |
| 12.6 | 0.543 | 203.0 | 132.9 | 167.9 | 45.6 | 10.1 |
| 22.3 | 0.607 | 323.2 | 219.7 | 271.4 | 80.8 | 25.6 |
| 15.3 | 0.543 | 273.1 | 188.2 | 230.7 | 70.8 | 19.5 |
| 13.0 | 0.574 | 247.3 | 172.2 | 209.7 | 65.8 | 16.3 |
| 22.3 | 0.656 | 302.2 | 231.4 | 266.8 | 101.5 | 24.9 |
| 12.0 | 0.525 | 213.0 | 143.3 | 178.1 | 51.7 | 11.6 |
| 25.0 | 0.618 | 280.2 | 206.0 | 243.1 | 85.5 | 21.3 |
| 13.3 | 0.559 | 176.3 | 104.3 | 140.3 | 28.5 | 6.0 |
| 19.3 | 0.564 | 236.2 | 163.7 | 200.0 | 62.1 | 14.9 |
| 23.6 | 0.588 | 252.4 | 188.1 | 220.3 | 79.6 | 17.9 |
| 11.3 | 0.542 | 194.9 | 131.2 | 163.0 | 47.3 | 9.4 |
| 18.3 | 0.570 | 251.4 | 182.9 | 217.2 | 74.8 | 17.5 |
| 21.0 | 0.612 | 272.2 | 204.3 | 238.3 | 87.3 | 20.6 |
| 21.3 | 0.564 | 292.9 | 241.1 | 267.0 | 115.1 | 24.9 |
| 18.0 | 0.521 | 254.0 | 189.2 | 221.6 | 80.0 | 18.1 |
| 25.3 | 0.619 | 298.9 | 253.2 | 276.1 | 124.7 | 26.3 |
| 18.0 | 0.541 | 259.3 | 170.9 | 215.1 | 59.4 | 17.1 |
| 15.6 | 0.527 | 239.6 | 174.0 | 206.8 | 71.0 | 15.9 |
| 22.0 | 0.563 | 271.4 | 191.0 | 231.2 | 74.3 | 19.6 |
| 20.3 | 0.602 | 310.3 | 212.9 | 261.6 | 79.4 | 24.1 |
| 11.6 | 0.581 | 216.3 | 144.7 | 180.5 | 51.7 | 12.0 |
| 25.3 | 0.512 | 285.2 | 238.9 | 262.0 | 116.2 | 24.2 |
| 14.3 | 0.554 | 239.5 | 165.0 | 202.2 | 62.0 | 15.2 |
| 5.6 | 0.571 | 157.9 | 83.4 | 120.7 | 15.5 | 3.0 |
| 16.6 | 0.609 | 274.5 | 200.4 | 237.5 | 82.4 | 20.5 |
| 19.0 | 0.521 | 254.7 | 174.7 | 214.7 | 65.2 | 17.1 |
| 13.3 | 0.548 | 228.5 | 159.2 | 193.8 | 61.0 | 14.0 |
| 20.6 | 0.541 | 254.8 | 200.7 | 227.7 | 91.2 | 19.0 |
| 14.3 | 0.600 | 235.3 | 181.0 | 208.2 | 79.8 | 16.1 |
| 15.0 | 0.593 | 261.0 | 183.9 | 222.5 | 71.7 | 18.3 |
| 18.6 | 0.547 | 262.4 | 198.8 | 230.6 | 86.0 | 19.5 |
| 18.6 | 0.639 | 292.9 | 225.9 | 259.4 | 100.0 | 23.8 |
| 7.0 | 0.529 | 184.0 | 111.4 | 147.7 | 32.3 | 7.1 |
| 10.3 | 0.526 | 210.7 | 141.3 | 176.0 | 50.7 | 11.3 |
| 17.6 | 0.500 | 243.2 | 176.1 | 209.6 | 71.5 | 16.3 |
| 12.6 | 0.531 | 226.8 | 139.3 | 183.0 | 41.8 | 12.4 |
| 19.6 | 0.541 | 240.9 | 178.4 | 209.7 | 74.8 | 16.3 |
| 25.6 | 0.591 | 313.6 | 258.7 | 286.2 | 123.9 | 27.8 |
| 15.3 | 0.492 | 210.8 | 162.7 | 186.8 | 72.1 | 12.9 |
| 26.3 | 0.604 | 339.3 | 269.3 | 304.3 | 123.4 | 30.5 |
| 18.6 | 0.508 | 249.9 | 189.4 | 219.7 | 82.0 | 17.8 |
| 6.3 | 0.493 | 164.5 | 93.7 | 129.1 | 22.9 | 4.3 |
| 16.6 | 0.585 | 258.9 | 188.9 | 223.9 | 77.6 | 18.5 |
| 19.0 | 0.522 | 232.8 | 200.4 | 216.6 | 100.3 | 17.4 |
| 15.0 | 0.481 | 233.3 | 174.0 | 203.6 | 73.7 | 15.4 |
| 12.0 | 0.561 | 228.4 | 155.0 | 191.7 | 56.8 | 13.7 |
| 22.0 | 0.566 | 276.6 | 217.5 | 247.1 | 98.5 | 21.9 |
| 24.3 | 0.538 | 261.3 | 191.5 | 226.4 | 79.1 | 18.8 |
| 16.0 | 0.554 | 236.9 | 175.8 | 206.4 | 73.9 | 15.8 |
| 17.6 | 0.543 | 282.6 | 217.3 | 249.9 | 95.8 | 22.4 |
| 18.0 | 0.541 | 237.0 | 179.6 | 208.3 | 77.7 | 16.1 |
| 15.0 | 0.493 | 242.1 | 175.3 | 208.7 | 71.2 | 16.2 |
| 17.0 | 0.616 | 263.1 | 186.6 | 224.8 | 73.5 | 18.6 |
| 28.3 | 0.534 | 294.3 | 247.0 | 270.6 | 120.5 | 25.5 |
| 18.3 | 0.575 | 265.5 | 196.0 | 230.7 | 81.8 | 19.5 |
| 21.0 | 0.499 | 269.1 | 217.6 | 243.3 | 101.9 | 21.4 |
| 21.3 | 0.591 | 266.8 | 206.7 | 236.8 | 91.9 | 20.4 |
| 17.3 | 0.478 | 250.5 | 178.9 | 214.7 | 71.2 | 17.1 |
| 10.3 | 0.575 | 200.4 | 136.3 | 168.3 | 50.1 | 10.2 |
| 20.0 | 0.651 | 245.7 | 162.0 | 203.8 | 56.3 | 15.5 |
| 13.3 | 0.499 | 207.0 | 149.3 | 178.1 | 60.3 | 11.6 |
| 18.0 | 0.535 | 255.4 | 184.6 | 220.0 | 74.8 | 17.9 |
| 17.0 | 0.576 | 263.9 | 179.8 | 221.9 | 66.3 | 18.2 |
| 16.6 | 0.594 | 250.7 | 170.1 | 210.4 | 62.3 | 16.5 |
| 20.6 | 0.594 | 288.7 | 216.3 | 252.5 | 92.2 | 22.7 |
| 5.3 | 0.523 | 145.8 | 88.1 | 116.9 | 25.4 | 2.5 |
| 18.0 | 0.557 | 254.9 | 193.8 | 224.3 | 84.2 | 18.5 |
| 4.3 | 0.539 | 163.6 | 94.6 | 129.1 | 24.2 | 4.3 |
| 3.6 | 0.559 | 177.3 | 85.6 | 131.4 | 9.4 | 4.6 |
| 23.0 | 0.563 | 304.3 | 216.6 | 260.4 | 85.8 | 23.9 |
| 12.6 | 0.499 | 212.9 | 139.5 | 176.2 | 48.0 | 11.3 |
| 20.3 | 0.499 | 242.1 | 200.7 | 221.4 | 96.6 | 18.1 |
| 22.3 | 0.628 | 304.3 | 236.5 | 270.4 | 105.7 | 25.4 |
| 27.3 | 0.526 | 289.3 | 228.9 | 259.1 | 104.5 | 23.7 |
| 14.0 | 0.588 | 235.8 | 156.0 | 195.9 | 54.6 | 14.3 |
| 16.0 | 0.570 | 247.4 | 180.2 | 213.8 | 73.8 | 17.0 |
| 17.3 | 0.535 | 258.6 | 193.7 | 226.2 | 82.5 | 18.8 |
| 20.3 | 0.616 | 261.5 | 155.7 | 208.6 | 43.3 | 16.2 |
| 6.3 | 0.570 | 181.8 | 112.5 | 147.1 | 34.4 | 7.0 |
| 16.3 | 0.536 | 236.0 | 166.5 | 201.3 | 65.0 | 15.1 |
| 18.0 | 0.568 | 240.1 | 168.2 | 204.2 | 65.0 | 15.5 |
| 13.0 | 0.518 | 219.7 | 148.7 | 184.2 | 54.2 | 12.5 |
| 22.6 | 0.571 | 287.6 | 255.3 | 271.4 | 131.6 | 25.6 |
| 9.0 | 0.544 | 210.1 | 148.9 | 179.5 | 58.6 | 11.8 |
| 12.3 | 0.505 | 195.1 | 137.6 | 166.4 | 53.7 | 9.9 |
| 26.3 | 0.649 | 369.0 | 281.3 | 325.2 | 122.6 | 33.6 |
| 17.6 | 0.560 | 242.8 | 168.5 | 205.6 | 64.1 | 15.7 |
| 13.3 | 0.530 | 208.6 | 141.1 | 174.8 | 51.4 | 11.1 |
| 20.6 | 0.600 | 265.0 | 180.3 | 222.6 | 66.4 | 18.3 |

TABLE III-continued

| GAT (mmHg) | CCT - (mm) | P1 - (count) | P2 - (count) | (P1 + P2)/2 (count) | P2 - .43 * P1 (count) | IOPG (mmHg) |
|---|---|---|---|---|---|---|
| 12.0 | 0.588 | 220.4 | 131.9 | 176.2 | 37.2 | 11.3 |
| 20.3 | 0.557 | 244.5 | 180.8 | 212.7 | 75.6 | 16.8 |
| 10.6 | 0.565 | 200.3 | 118.3 | 159.3 | 32.2 | 8.8 |
| 16.3 | 0.525 | 237.7 | 177.2 | 207.4 | 75.0 | 16.0 |
| 57.6 | 0.607 | 518.6 | 495.3 | 507.0 | 272.3 | 60.8 |
| 25.3 | 0.558 | 290.0 | 209.6 | 249.8 | 84.9 | 22.3 |
| 21.3 | 0.561 | 271.1 | 189.7 | 230.4 | 73.1 | 19.4 |
| 15.6 | 0.586 | 241.4 | 165.9 | 203.6 | 62.1 | 15.4 |
| 17.3 | 0.503 | 237.6 | 178.0 | 207.8 | 75.9 | 16.1 |
| 16.6 | 0.513 | 203.1 | 124.2 | 163.6 | 36.9 | 9.5 |
| 21.0 | 0.545 | 283.4 | 215.3 | 249.3 | 93.5 | 22.3 |
| 15.6 | 0.591 | 245.9 | 165.2 | 205.6 | 59.4 | 15.7 |
| 20.3 | 0.541 | 261.5 | 203.8 | 232.7 | 91.4 | 19.8 |
| 17.3 | 0.528 | 225.8 | 159.5 | 192.7 | 62.4 | 13.8 |
| 17.0 | 0.553 | 271.0 | 188.9 | 230.0 | 72.4 | 19.4 |
| 16.0 | 0.477 | 199.6 | 143.7 | 171.7 | 57.9 | 10.7 |
| 15.3 | 0.635 | 250.0 | 193.5 | 221.8 | 86.1 | 18.1 |
| 15.3 | 0.476 | 207.2 | 153.0 | 180.1 | 63.9 | 11.9 |
| 12.0 | 0.575 | 187.4 | 140.7 | 164.0 | 60.1 | 9.5 |
| 27.3 | 0.603 | 323.1 | 257.2 | 290.1 | 118.3 | 28.4 |
| 24.6 | 0.607 | 306.7 | 266.6 | 286.7 | 134.8 | 27.8 |
| 28.3 | 0.594 | 327.8 | 274.5 | 301.1 | 133.6 | 30.0 |
| 22.6 | 0.574 | 272.6 | 184.0 | 228.3 | 66.8 | 19.1 |
| 19.3 | 0.523 | 230.5 | 156.8 | 193.6 | 57.6 | 13.9 |
| 18.3 | 0.588 | 280.2 | 222.7 | 251.4 | 102.2 | 22.6 |
| 21.3 | 0.606 | 261.6 | 170.7 | 216.1 | 58.2 | 17.3 |
| 27.0 | 0.575 | 289.6 | 234.7 | 262.2 | 110.2 | 24.2 |
| 22.0 | 0.522 | 290.1 | 225.1 | 257.6 | 100.4 | 23.5 |
| 21.3 | 0.511 | 269.4 | 208.6 | 239.0 | 92.7 | 20.7 |
| 25.0 | 0.478 | 292.4 | 245.4 | 268.9 | 119.6 | 25.2 |
| 3.3 | 0.608 | 151.2 | 64.6 | 107.9 | −0.4 | 1.1 |
| 21.0 | 0.666 | 248.2 | 209.9 | 229.1 | 103.2 | 19.2 |
| 24.3 | 0.566 | 298.3 | 246.6 | 272.4 | 118.3 | 25.7 |
| 30.0 | 0.601 | 342.6 | 267.7 | 305.1 | 120.4 | 30.6 |
| 20.0 | 0.517 | 246.2 | 189.2 | 217.7 | 83.3 | 17.5 |
| 18.3 | 0.587 | 231.1 | 162.4 | 196.8 | 63.1 | 14.4 |
| 21.3 | 0.610 | 280.8 | 201.4 | 241.1 | 80.6 | 21.0 |
| 14.3 | 0.559 | 257.1 | 204.8 | 231.0 | 94.3 | 19.5 |
| 14.0 | 0.572 | 223.1 | 148.9 | 186.0 | 53.0 | 12.8 |
| 17.3 | 0.534 | 236.2 | 170.9 | 203.5 | 69.3 | 15.4 |
| 22.6 | 0.541 | 277.4 | 198.0 | 237.7 | 78.7 | 20.5 |
| 19.0 | 0.589 | 268.0 | 188.8 | 228.4 | 73.6 | 19.1 |
| 13.3 | 0.500 | 209.7 | 165.8 | 187.8 | 75.6 | 13.1 |
| 5.6 | 0.582 | 188.6 | 118.2 | 153.4 | 37.1 | 7.9 |
| 20.3 | 0.524 | 240.7 | 181.8 | 211.2 | 78.3 | 16.6 |
| 22.3 | 0.592 | 287.7 | 218.3 | 253.0 | 94.5 | 22.8 |
| 15.3 | 0.576 | 259.1 | 180.8 | 219.9 | 69.4 | 17.9 |
| 19.0 | 0.564 | 243.4 | 187.4 | 215.4 | 82.7 | 17.2 |
| 14.0 | 0.556 | 249.5 | 163.7 | 206.6 | 56.4 | 15.9 |
| 10.3 | 0.499 | 192.5 | 127.1 | 159.7 | 44.5 | 8.9 |
| 20.0 | 0.580 | 215.7 | 134.7 | 175.2 | 41.9 | 11.2 |
| 18.3 | 0.470 | 258.0 | 224.6 | 241.3 | 113.7 | 21.1 |
| 13.0 | 0.544 | 225.8 | 161.5 | 193.6 | 64.4 | 13.9 |
| 13.6 | 0.577 | 242.0 | 169.6 | 205.8 | 65.6 | 15.8 |
| 20.6 | 0.606 | 220.5 | 197.8 | 209.1 | 102.9 | 16.3 |
| 31.6 | 0.541 | 303.6 | 225.8 | 264.7 | 95.3 | 24.6 |
| 30.3 | 0.581 | 356.1 | 291.9 | 324.0 | 138.8 | 33.4 |
| 24.0 | 0.560 | 288.9 | 211.5 | 250.2 | 87.3 | 22.4 |
| 18.0 | 0.581 | 243.3 | 194.0 | 218.6 | 89.4 | 17.7 |
| 20.6 | 0.536 | 248.4 | 186.3 | 217.4 | 79.5 | 17.5 |
| 37.0 | 0.516 | 328.8 | 277.0 | 302.9 | 135.7 | 30.3 |
| 15.3 | 0.547 | 211.7 | 125.0 | 168.3 | 33.9 | 10.2 |
| 16.6 | 0.563 | 241.6 | 177.9 | 209.8 | 74.1 | 16.4 |
| 10.6 | 0.501 | 212.1 | 139.9 | 176.0 | 48.7 | 11.3 |
| 18.6 | 0.594 | 277.3 | 207.5 | 242.4 | 88.2 | 21.2 |
| 18.0 | 0.564 | 256.3 | 180.5 | 218.4 | 70.3 | 17.6 |
| 9.6 | 0.549 | 213.2 | 125.5 | 169.3 | 33.8 | 10.3 |
| 14.6 | 0.518 | 211.0 | 139.4 | 175.2 | 48.7 | 11.2 |
| 18.3 | 0.556 | 233.1 | 166.0 | 199.5 | 65.8 | 14.8 |
| 19.3 | 0.571 | 253.5 | 172.5 | 213.0 | 63.5 | 16.8 |
| 20.3 | 0.494 | 242.6 | 164.6 | 203.6 | 60.3 | 15.4 |
| 23.3 | 0.575 | 298.9 | 193.3 | 246.1 | 64.8 | 21.8 |
| 20.0 | 0.583 | 249.4 | 168.3 | 208.8 | 61.1 | 16.2 |
| 19.0 | 0.538 | 261.6 | 192.2 | 226.9 | 79.7 | 18.9 |
| 18.3 | 0.509 | 247.6 | 205.5 | 226.6 | 99.0 | 18.9 |
| 12.6 | 0.596 | 251.1 | 167.0 | 209.0 | 59.0 | 16.2 |
| 20.6 | 0.552 | 284.2 | 226.2 | 255.2 | 104.0 | 23.1 |
| 17.6 | 0.634 | 269.4 | 204.6 | 237.0 | 88.8 | 20.4 |
| 16.3 | 0.536 | 236.1 | 153.3 | 194.7 | 51.8 | 14.1 |
| 12.6 | 0.616 | 259.9 | 211.0 | 235.4 | 99.3 | 20.2 |
| 10.0 | 0.493 | 178.4 | 113.9 | 146.2 | 37.2 | 6.8 |
| 19.3 | 0.570 | 250.6 | 176.0 | 213.3 | 68.2 | 16.9 |
| 19.0 | 0.554 | 259.5 | 184.5 | 222.0 | 73.0 | 18.2 |
| 13.6 | 0.554 | 213.2 | 147.8 | 180.5 | 56.2 | 12.0 |
| 23.0 | 0.603 | 324.6 | 220.6 | 272.6 | 81.1 | 25.7 |
| 19.6 | 0.549 | 271.8 | 187.7 | 229.7 | 70.8 | 19.3 |
| 14.0 | 0.578 | 262.8 | 168.1 | 215.4 | 55.1 | 17.2 |
| 24.3 | 0.678 | 307.0 | 263.9 | 285.5 | 131.9 | 27.7 |
| 11.0 | 0.536 | 215.7 | 139.4 | 177.6 | 46.6 | 11.5 |
| 29.0 | 0.610 | 291.1 | 232.3 | 261.7 | 107.1 | 24.1 |
| 13.3 | 0.519 | 192.4 | 119.6 | 156.0 | 36.9 | 8.3 |
| 15.6 | 0.582 | 207.1 | 131.5 | 169.3 | 42.5 | 10.3 |
| 21.6 | 0.570 | 261.0 | 185.8 | 223.4 | 73.6 | 18.4 |
| 14.6 | 0.562 | 216.8 | 152.8 | 184.8 | 59.6 | 12.6 |
| 19.3 | 0.569 | 247.0 | 180.2 | 213.6 | 74.0 | 16.9 |
| 22.0 | 0.627 | 298.4 | 226.4 | 262.4 | 98.1 | 24.2 |
| 18.3 | 0.536 | 305.7 | 191.2 | 248.5 | 59.7 | 22.1 |
| 20.6 | 0.523 | 268.5 | 215.4 | 242.0 | 99.9 | 21.2 |
| 22.6 | 0.616 | 288.6 | 249.7 | 269.1 | 125.6 | 25.2 |
| 20.0 | 0.539 | 239.4 | 155.9 | 197.6 | 53.0 | 14.5 |
| 16.3 | 0.539 | 230.8 | 162.3 | 196.6 | 63.1 | 14.4 |
| 25.0 | 0.560 | 239.1 | 158.8 | 199.0 | 56.0 | 14.7 |
| 22.6 | 0.617 | 326.7 | 219.2 | 273.0 | 78.8 | 25.8 |
| 16.6 | 0.599 | 277.5 | 188.9 | 233.2 | 69.6 | 19.9 |
| 19.6 | 0.526 | 223.0 | 167.4 | 195.2 | 71.6 | 14.2 |
| 14.3 | 0.544 | 242.1 | 173.2 | 207.7 | 69.1 | 16.0 |
| 20.0 | 0.557 | 275.3 | 207.5 | 241.4 | 89.1 | 21.1 |
| 9.6 | 0.621 | 205.4 | 117.9 | 161.7 | 29.6 | 9.2 |
| 19.0 | 0.525 | 247.6 | 155.3 | 201.5 | 48.8 | 15.1 |
| 14.6 | 0.558 | 226.9 | 150.2 | 188.5 | 52.6 | 13.2 |
| 22.6 | 0.522 | 276.4 | 206.3 | 241.3 | 87.4 | 21.1 |
| 15.6 | 0.596 | 239.6 | 179.7 | 209.6 | 76.7 | 16.3 |
| 15.3 | 0.596 | 262.4 | 179.2 | 220.8 | 66.4 | 18.0 |
| 34.6 | 0.539 | 345.8 | 305.2 | 325.5 | 156.5 | 33.7 |
| 21.6 | 0.599 | 314.8 | 247.2 | 281.0 | 111.8 | 27.0 |
| 10.0 | 0.515 | 211.5 | 143.6 | 177.6 | 52.7 | 11.5 |
| 14.6 | 0.499 | 247.4 | 188.7 | 218.1 | 82.3 | 17.6 |
| 18.3 | 0.532 | 263.1 | 191.2 | 227.2 | 78.0 | 19.0 |
| 18.6 | 0.527 | 247.5 | 175.1 | 211.3 | 68.7 | 16.6 |
| 32.3 | 0.593 | 343.3 | 274.9 | 309.1 | 127.3 | 31.2 |
| 17.6 | 0.513 | 214.4 | 162.6 | 188.5 | 70.4 | 13.2 |
| 24.3 | 0.601 | 307.7 | 241.7 | 274.7 | 109.3 | 26.1 |
| 16.6 | 0.500 | 238.2 | 174.2 | 206.2 | 71.8 | 15.8 |
| 16.3 | 0.477 | 200.0 | 148.0 | 174.0 | 62.0 | 11.0 |
| 15.0 | 0.574 | 270.4 | 173.9 | 222.2 | 57.7 | 18.2 |
| 16.6 | 0.513 | 223.9 | 158.7 | 191.3 | 62.5 | 13.6 |
| 16.0 | 0.494 | 258.9 | 196.1 | 227.5 | 84.8 | 19.0 |
| 17.0 | 0.563 | 268.6 | 186.7 | 227.6 | 71.2 | 19.0 |
| 23.6 | 0.567 | 269.4 | 205.5 | 237.4 | 89.7 | 20.5 |
| 18.6 | 0.523 | 260.7 | 182.9 | 221.8 | 70.8 | 18.2 |
| 11.3 | 0.526 | 206.3 | 137.8 | 172.1 | 49.1 | 10.7 |
| 20.6 | 0.547 | 280.3 | 209.3 | 244.8 | 88.8 | 21.6 |
| 21.6 | 0.560 | 258.3 | 199.1 | 228.7 | 88.1 | 19.2 |
| 14.3 | 0.490 | 229.1 | 175.1 | 202.1 | 76.6 | 15.2 |
| 14.3 | 0.592 | 258.5 | 182.5 | 220.5 | 71.3 | 18.0 |
| 23.3 | 0.533 | 270.2 | 187.0 | 228.6 | 70.8 | 19.2 |
| 18.3 | 0.572 | 252.2 | 173.9 | 213.1 | 65.5 | 16.9 |
| 20.0 | 0.504 | 246.0 | 193.7 | 219.9 | 88.0 | 17.9 |
| 21.3 | 0.573 | 283.9 | 211.7 | 247.8 | 89.6 | 22.0 |
| 17.0 | 0.476 | 240.1 | 164.2 | 202.2 | 61.0 | 15.2 |
| 39.0 | 0.566 | 377.8 | 338.3 | 358.1 | 175.9 | 38.5 |
| 15.0 | 0.506 | 206.0 | 134.6 | 170.3 | 46.0 | 10.5 |
| 19.3 | 0.534 | 254.5 | 188.3 | 221.4 | 78.9 | 18.1 |
| 15.6 | 0.576 | 281.4 | 202.0 | 241.7 | 81.0 | 21.1 |
| 21.6 | 0.611 | 301.2 | 238.2 | 269.7 | 108.6 | 25.3 |
| 19.6 | 0.609 | 272.5 | 207.9 | 240.2 | 90.7 | 20.9 |
| 24.6 | 0.516 | 269.2 | 214.8 | 242.0 | 99.1 | 21.2 |
| 17.6 | 0.562 | 259.6 | 185.8 | 222.7 | 74.2 | 18.3 |
| 20.0 | 0.546 | 255.8 | 196.2 | 226.0 | 86.2 | 18.8 |
| 17.3 | 0.544 | 260.5 | 171.8 | 216.1 | 59.8 | 17.3 |
| 22.0 | 0.557 | 289.8 | 203.2 | 246.5 | 78.5 | 21.8 |
| 13.6 | 0.513 | 215.8 | 142.4 | 179.1 | 49.6 | 11.8 |

TABLE III-continued

| GAT (mmHg) | CCT (mm) | P1 (count) | P2 (count) | (P1 + P2)/2 (count) | P2 − .43 * P1 (count) | IOPG (mmHg) |
|---|---|---|---|---|---|---|
| 13.6 | 0.486 | 196.6 | 138.9 | 167.7 | 54.4 | 10.1 |
| 29.0 | 0.624 | 348.8 | 295.2 | 322.0 | 145.2 | 33.1 |
| 25.6 | 0.542 | 309.6 | 255.2 | 282.4 | 122.1 | 27.2 |
| 16.0 | 0.581 | 243.0 | 178.5 | 210.8 | 74.0 | 16.5 |
| 12.3 | 0.592 | 249.6 | 179.0 | 214.3 | 71.7 | 17.0 |
| 21.0 | 0.534 | 264.2 | 208.6 | 236.4 | 94.9 | 20.3 |
| 19.0 | 0.611 | 261.1 | 167.9 | 214.5 | 55.7 | 17.1 |
| 8.6 | 0.582 | 176.5 | 100.9 | 138.7 | 25.1 | 5.7 |
| 16.6 | 0.528 | 242.5 | 175.5 | 209.0 | 71.2 | 16.2 |
| 18.0 | 0.573 | 228.8 | 158.1 | 193.4 | 59.8 | 13.9 |
| 18.3 | 0.518 | 241.2 | 179.8 | 210.5 | 76.1 | 16.5 |
| 23.3 | 0.566 | 310.2 | 236.8 | 273.5 | 103.4 | 25.9 |
| 9.6 | 0.526 | 184.4 | 127.9 | 156.2 | 48.6 | 8.3 |
| 5.6 | 0.379 | 140.0 | 84.5 | 112.2 | 24.3 | 1.8 |
| 22.6 | 0.651 | 304.5 | 247.4 | 275.9 | 116.5 | 26.2 |
| 4.0 | 0.543 | 152.3 | 69.0 | 110.7 | 3.5 | 1.5 |
| 13.0 | 0.525 | 223.1 | 163.4 | 193.2 | 67.5 | 13.9 |
| 21.3 | 0.577 | 268.3 | 181.9 | 225.1 | 66.5 | 18.6 |
| 20.3 | 0.546 | 235.4 | 181.3 | 208.4 | 80.0 | 16.1 |
| 11.6 | 0.566 | 205.5 | 125.7 | 165.6 | 37.3 | 9.8 |
| 17.3 | 0.546 | 256.8 | 184.3 | 220.6 | 73.9 | 18.0 |
| 57.3 | 0.618 | 530.3 | 490.5 | 510.4 | 262.4 | 61.3 |
| 21.3 | 0.561 | 263.9 | 188.8 | 226.4 | 75.4 | 18.8 |
| 17.3 | 0.575 | 260.7 | 185.4 | 223.0 | 73.3 | 18.3 |
| 13.6 | 0.486 | 203.1 | 138.7 | 170.9 | 51.4 | 10.5 |
| 17.3 | 0.511 | 216.6 | 161.7 | 189.1 | 68.5 | 13.3 |
| 27.0 | 0.590 | 327.2 | 267.3 | 297.2 | 126.6 | 29.4 |
| 12.3 | 0.732 | 238.3 | 158.8 | 198.5 | 56.4 | 14.7 |
| 30.3 | 0.519 | 340.9 | 306.9 | 323.9 | 160.3 | 33.4 |
| 25.6 | 0.526 | 283.7 | 250.1 | 266.9 | 128.1 | 24.9 |
| 17.6 | 0.548 | 276.6 | 187.5 | 232.0 | 68.5 | 19.7 |
| 14.0 | 0.457 | 207.9 | 161.8 | 184.8 | 72.4 | 12.6 |
| 18.3 | 0.612 | 277.3 | 210.7 | 244.0 | 91.5 | 21.5 |
| 12.6 | 0.519 | 218.8 | 152.4 | 185.6 | 58.4 | 12.7 |
| 18.6 | 0.594 | 264.2 | 197.3 | 230.7 | 83.7 | 19.5 |
| 25.0 | 0.601 | 287.8 | 226.3 | 257.1 | 102.5 | 23.4 |
| 25.3 | 0.615 | 301.6 | 239.0 | 270.3 | 109.3 | 25.4 |
| 35.6 | 0.598 | 368.5 | 323.3 | 345.9 | 164.9 | 36.7 |
| 20.0 | 0.531 | 229.7 | 150.5 | 190.1 | 51.7 | 13.4 |

What is claimed is:

1. A non-contact tonometer comprising:
   a fluid pump including a plenum chamber;
   a fluid discharge tube in communication with the pump for directing a fluid pulse at a cornea of a patient to cause reversible deformation of the cornea from an original state of convexity through a first state of applanation to a state of concavity, and back through a second state of applanation to the state of convexity;
   an applanation detector providing an applanation signal indicating a time of the first state of applanation and a time of the second state of applanation;
   a pressure sensor arranged to provide a pressure signal indicating fluid pressure in the plenum chamber as a function of time;
   a processor connected to the applanation detector and the pressure sensor for evaluating the applanation signal and the pressure signal to provide a first pressure value (P1) coinciding with the first state of applanation and a second pressure value coinciding with the second state of applanation, and for calculating an intraocular pressure value using a predetermined function of the first pressure value (P1) and the second pressure value (P2), wherein the predetermined function is empirically derived to minimize cornea-related influence on the intraocular pressure value; and
   a memory connected to the processor, wherein the memory stores the empirically derived predetermined function;
   wherein the predetermined function is derived from empirical data measuring the first pressure value (P1) and the second pressure value (P2) both before and after surgical alteration of the cornea.

2. The non-contact tonometer according to claim 1, wherein the predetermined function is optimized, at least in part, to minimize change in the calculated intraocular pressure value between measurements made before surgical alteration of the cornea and measurements made after surgical alteration of the cornea.

3. The non-contact tonometer according to claim 1, wherein the predetermined function is optimized, at least in part, to minimize statistical correlation between the calculated intraocular pressure value and central corneal thickness.

4. The non-contact tonometer according to claim 1, wherein the predetermined function is a linear function.

5. The non-contact tonometer according to claim 4, wherein the predetermined function is expressible as $$IOP = K_1 * (F * P1 + P2) + K_2$$

wherein F~−0.43, and $K_1$ and $K_2$ are constants.

6. A method of deriving a function for calculating intraocular pressure of an eye comprising the steps of:
   (A) referencing empirical data taken with respect to a plurality of eyes, the empirical data measuring a first pressure value (P1) associated with a first applanation of a cornea during a reversible deformation of the cornea and a second pressure value (P2) associated with a second applanation of the cornea during the reversible deformation, the first and second pressure values (P1 and P2) being obtained both before and after surgical alteration of the cornea for each of the plurality of eyes;
   (B) choosing a form of the function wherein the first pressure value (P1) and the second pressure value (P2) are independently weighted variables; and
   (C) determining relative weights of the first and second pressure values (P1 and P2) so as to minimize change in the intraocular pressure value between measurements made before surgical alteration of the cornea and measurements made after surgical alteration of the cornea.

7. The method according to claim 6, wherein the surgical alteration of the cornea includes a LASIK procedure.

* * * * *